United States Patent [19]
Komiyama et al.

[11] Patent Number: 4,512,968
[45] Date of Patent: Apr. 23, 1985

[54] ORAL COMPOSITIONS

[75] Inventors: Noboru Komiyama, Tokyo; Hiroshi Itoi, Kamagaya; Hiroshi Sano, Hachioji, all of Japan

[73] Assignee: Lion Corporation, Tokyo, Japan

[21] Appl. No.: 555,111

[22] Filed: Nov. 23, 1983

[30] Foreign Application Priority Data

Nov. 30, 1982 [JP] Japan .............................. 57-210817
Feb. 18, 1983 [JP] Japan .............................. 58-24853

[51] Int. Cl.³ .......................... A61K 9/68; A61K 7/16; A61K 7/22; A61K 31/715
[52] U.S. Cl. ........................................ 424/48; 424/49; 424/54; 514/55
[58] Field of Search .................................. 424/48–58, 424/180

[56] References Cited
FOREIGN PATENT DOCUMENTS
57323 8/1982 European Pat. Off.
55-69506 5/1980 Japan .

OTHER PUBLICATIONS

Roberts et al., Chem. Abstr. 93, #143815a, (1980) of Scand. J. Dent. Res. 88(3): 201–9, (1980), Effects of 2-Deoxy-D-Glucose and Other Sugar Analogs on Acid Production from Sugars by Human Dental Plaque Bacteria.
Sunstar, Chem. Abstr. 93, #191921d, (1980) of Jpn. Kokai Tokkyo Kotto 80 69506, May 26, 1980.
Dills, Chem. Abstr. 97, #168734a, (1982) of Eur. Pat. Appl. EP 57323, Aug. 11, 1982.
Merck Index, 9th Ed., (1976), Rahway, N.J., p. 259, #2021, "Chitin", (predominantly N-Acetyl-D-Glucosamine); p. 576, #4289, Glucosamine, (N-Acetyl-D-Glucosamine).

Primary Examiner—Shep K. Rose
Attorney, Agent, or Firm—Flynn, Thiel, Boutell & Tanis

[57] ABSTRACT

Chitin or chitin derivatives compounded with oral compositions such as dentifrice, mouth rinse, oral freshener, chewing gum and the like exhibit superior medicine effects for the prevention of dental caries, periodontoclasia and mouth odor. And, chitosan salt is also effective as the binding agent for use in the above mentioned oral compositions.

10 Claims, 1 Drawing Figure

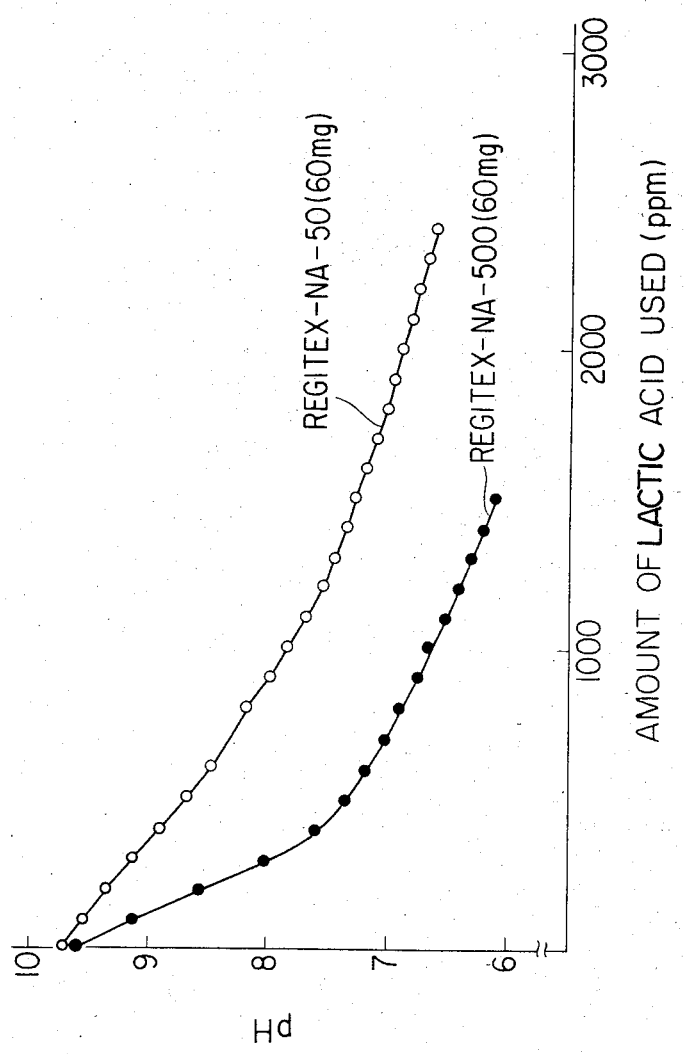

ORAL COMPOSITIONS

BACKGROUND OF THE INVENTION

The present invention relates to oral compositions compounded with chitin or its derivatives.

It has usually been practiced to prevent the occurrence of dental caries, periodontoclasia and mouth odor by compounding effective ingredients such as sodium monofluorophosphate, $\epsilon$-aminocaproic acid, chlorhexidine hydrochloride and the like with oral compositions including dentifrices such as tooth paste, tooth powder, liquid dentifrice and the like; mouth rinses; oral fresheners and chewing gums. However, the oral compositions have been disadvantageous in that as a rule they are all ejected after use and the dentifrices are commonly washed out with water after use, and therefore the amounts of said effective ingredients to be compounded must be increased considerably in order to expect the effective ingredients to achieve their inherent effects.

Although tin fluoride, phytic acid and the like are used frequently as the effective ingredients in the dentifrices, and insoluble metaphosphate, sodium pyrophosphate, silica (amorphous silicic anhydride) and the like are used frequently as abrasives therein, it is preferable that the dentifrices compounded with them are held acidic as a whole because they are generally stable on the acidic side, and accordingly it is more preferable that the binding agents used in the dentifrices are not only stable on the acidic side but also are acidic themselves in situ.

As the binding agents there have usually been used Veegum, carboxymethyl cellulose, polyvinyl alcohol, carrageenan and the like. However, these are apt to be influenced by the water-soluble salt compounded in the dentifrice and lose their binding ability. In case their binding ability is lost, there are brought about the following disadvantages such as deterioration in viscosity of the dentifrice and lowering of water-holding capacity, while in the case of tooth paste the smoothness of the surface is lost and the water content comes to separate.

In addition thereto, when silica is compounded, as abrasives, with the tooth paste, it normally displays a rough taste due to impurities contained in the silica. Because of this, it has usually been necessary to cover up the rough taste by adding special or very strong flavoring.

SUMMARY OF THE INVENTION

The present invention provides oral compositions including dentifrices, mouth rinses, oral fresheners and chewing gums compounded with chitin or its derivatives.

The chitin derivatives referred to herein denote chitosan (deacetylated product of chitin) and inorganic and organic acid salts of chitosan. The chitin or chitosan compounded with the oral compositions effectively prevents the occurrence of dental caries, periodontoclasia and mouth odor, and inorganic and organic acid salts of chitosan function as exceedingly superior binding agents for the oral compositions and simultaneously exhibit a superior effect in preventing periodontoclasia. Furthermore, these chitosan salts are also capable of covering up the rough taste originating from the silica mixed in the dentifrice.

BRIEF DESCRIPTION OF THE DRAWING

The accompanying drawing is a graph illustrating the experimental results about the lactic acid neutralizing ability of chitosan obtained in Experimental Example 1 referred to afterwards.

DETAILED DESCRIPTION OF THE INVENTION

Chitin which is present in the shells of arthropoda, the bones of mollusca and the mycelium and spores of molds and chitosan which is a deacetylated product of said chitin, are similar in chemical structure to cellulose, but are by far superior in the resistance to chemicals as compared with cellulose, and are possessed of a variety of attractive characteristics because chitin and chitosan have acetamide and amino groups in the molecules. However, the fact is that chitin and chitosan are exceedingly low in utilization degree as compared with cellulose and other polysaccharides.

Chitin can be obtained, in the known manner, from the organic bone substances of arthropoda and mollusca or the mycelium and spores of molds. For instance, when obtaining chitin from the shells of crabs, lobsters, Euphasiacea and the like, the shells are pulverized and then treated with hydrochloric acid for removing calcium carbonate, furthermore treated with caustic soda for removing protein and other foreign elements, washed with water, and dried. Thus, a white amorphous powdery chitin can be obtained. On the other hand, chitosan can be obtained in the form of a white amorphous powder by treating chitin with alkali for deacetylation.

Chitosan per se is water-insoluble. However, it forms salts together with hydrochloric acid and other acids and solves in water. Therefore, in the preparation of chitosan salt, it is profitable to dissolve chitosan in a dilute aqueous solution of an inorganic acid such as hydrochloric acid, phosphoric acid and the like or in a dilute aqueous solution of an organic acid such as acetic, propionic, oxalic, malonic, succinic, maleic, adipic, lactic, pyruvic, malic, tartaric, citric and ascorbic acids, alkylbenzene-sulphonic acid having $C_{10}$-$C_{20}$ alkyl, aliphatic olefin sulphonic acid having 10–20 carbon atoms, mono- or di-alkylphosphates having 10–20 carbon atoms and the like.

The chitin and chitosan used in the present invention need not always be obtained from shells and the like, because these are commercially available, for instance the chitin and chitosan prepared and sold in the trade name "REGITEX" by Nanyo Kasei K.K. in Japan can be used in the present invention.

In this connection, it is added that the standard of differentiating chitin from chitosan in the present invention is that chitosan has 60% or more of deacetylation degree, while chitin is less than 60%.

In the oral composition according to the present invention, it is necessary that the amount of chitin and/or chitosan compounded should be at least 0.01 wt.% for the purpose of having the oral composition exhibit the effect of chitin or chitosan, but the allowable compounding amount differs depending on the kind of each oral composition. In this connection, it is to be noted that in the case of tooth paste, said amount is 0.01–70 wt.%, preferably 0.05–50 wt.%, and when it is in excess of 70 wt.% there is the possibility of the formability being damaged at the time of extrusion from the tube.

In the case of tooth powder, the compounding amount is 0.01–97 wt.%, preferably 0.05–95 wt.%, and when it is in excess of 97 wt.% it is undesirable because the room for compounding the ingredients required for the dentifrice such as foaming agent, sweetening agent, perfume and the like is not left. In the case of solid oral freshener, chitin and/or chitosan is compounded in the amount of 0.01–70 wt.%, preferably 0.05–60 wt.%. In case said amount is in excess of 70 wt.%, it becomes difficult to granulate the solid oral freshener using liquid gum arabic and the like. In the case of liquid oral compositions such as liquid dentifrice, liquid mouth freshener, mouth rinse or the like, chitin and/or chitosan desirably should be compounded in the amount of 0.01–20 wt.%, preferably 0.05–20 wt.%. In case said amount is in excess of 20 wt.%, it is impossible to dissolve chitin and/or chitosan wholly into a liquid composition even if chitin and/or chitosan has been subjected to solubilizing treatment, and it is also impossible to obtain a practically usable liquid oral composition because the viscosity also increases. When compounding chitin and/or chitosan with chewing gum, the desirable compounding amount is 0.01–60 wt.%, preferably 0.05–50 wt.%. In case said amount is in excess of 60 wt.%, the formability required for gum is deteriorated and consequently the texture of chewing also becomes worse. When making the inorganic salt or organic salt of chitosan function as the binding agent for the oral composition, it is preferable that said salt is compounded in the range of 0.5–10 wt.% of the oral composition, while when making said salt function as only the ingredient effective for the prevention of periodontoclasia, its effects can be displayed when compounded in the amount of about 0.01 wt.% irrespective of the kind of oral composition.

In addition to the chitin and its derivatives used in the oral composition, the present invention can use any ingredients which have usually been used in the oral compositions, and there is no possibility that the use of other ingredients is restricted by the chitin or chitin derivatives to be compounded. For instance, in the dentifrice there can be used humectants such as glycerine, sorbitol, propylene glycol and the like; abrasives such as calcium hydrogen phosphate, calcium pyrophosphate, calcium carbonate, aluminum hydroxide, hydrated silica, anhydrous silica, calcium sulfate, magnesium phosphate, calcium sulfite, zeolite, insoluble sodium metaphosphate and the like; binding agents such as carboxymethylcellulose, carrageenan; anionic surface active agents such as α-sodium olefinsulfonate, sodium lauryl sulfate, lauric acid monoglyceride sulfate, acyl taurate, lauric acid monoglyceride sulfonate, lauryl sarcosinate and the like; nonionic surface active agents such as saccharide, monoglyceride stearate, lauryl diethanolamide, polyoxyethylene sorbitan monolaurate and the like; amphoteric surface active agents; perfumes such as menthol, anethole; sweetening materials; effective ingredients such as chlorhexidine hydrochloride, chlorhexidine gluconate, ε-amino caproic acid, dihydrocholestanol, tranexamic acid, allantoin, allantoinchlorohydroxy aluminum, sodium monofluorophosphate, dextranase, polyethylene glycol, sodium chloride and the like; preservatives; water and the like. Similarly, the oral freshener, mouth rinse and chewing gum can use the various kinds of ingredients, which have normally been used in these agents, together with chitin and/or chitin derivative. However, it is needless to say that since chitin and chitosan are effective for preventing dental caries, periodontoclasia and mouth odor and the chitosan salt is also effective for preventing periodontoclasia, the effective ingredients compounded in the conventional ingredients in expectation of those effects can be partly or wholly replaced by the chitin or its derivatives of the present invention.

Next, the effects of chitin and chitosan for preventing dental caries, periodontoclasia and mouth odor will be explained concretely with reference to experimental examples.

EXPERIMENTAL EXAMPLE 1

The present example and the following Experimental Example 2 are directed toward the effects of chitin and the like for preventing dental caries.

Chitosan REGITEX-NA-50 produced by Nanyo Kasei K.K. (molecular weight: 47000, deacetylation degree: 77%) and chitosan REGITEX-NA-500 produced by the same company (molecular weight: 114000, deacetylation degree: 60%) were pulverized respectively, and were sifted through a 200 mesh-sieve. The chitosan particles that passed through the sieve were tested. 60 mg of chitosan was measured correctly, and deionized water was added thereto so as to become 20 ml. The lactic acid neutralizing ability of the resulting sample was measured on the basis of the aqueous lactic acid solution (200 ppm) and by means of the bench pH meter (COM-10) produced by Denki Kagaku Keiki K.K. The obtained result is shown in the accompanying drawing. It is apparent from the drawing that the lactic acid neutralizing ability of REGITEX-NA-50 is 300 ppm/mg and that of REGITEX-NA-500 is 12 ppm/mg respectively.

EXPERIMENTAL EXAMPLE 2

1 g of tooth paste of Composition A referred to afterwards was placed on a toothbrush. The teeth were brushed for 3 minutes by the rolling teeth-brushing method, washed enough with water, thereafter the pH on the tongue was measured by means of the bench pH meter (glass flat electrode CE301S-OT) produced by Denki Kagaku Keiki K.K. As the control there was used the tooth paste of Composition A wherein, however, the chitosan was replaced by water. 10 grown-up men, whose pH values on the tongues were closely similar were chosen as subjects. The pH value on the tongue of each subject before teeth brushing is shown in Table 1.

As the result of teeth brushing, the pH value on the tongue becomes higher than before teeth brushing, and then decreases with lapse of time. Changes between the pH values before and after teeth brushing with lapse of time are shown in Table 2.

TABLE 1

| pH on tongue (before teeth brushing) | | | | | | | | | | Average | Standard deviation |
|---|---|---|---|---|---|---|---|---|---|---|---|
| 6.76 | 6.45 | 6.70 | 6.65 | 6.46 | 6.16 | 6.27 | 6.51 | 6.36 | 6.28 | 6.46 | 0.19 |

TABLE 2

| Time (min.) | ΔpH* Tooth paste | |
|---|---|---|
| | A of Example 1 | Control |
| Just after | 0.74 ± 0.10 | 0.35 ± 0.11 |
| 5 | 0.55 ± 0.21 | 0.28 ± 0.23 |
| 10 | 0.59 ± 0.20 | 0.16 ± 0.19 |
| 15 | 0.54 ± 0.18 | 0.04 ± 0.19 |
| 20 | 0.62 ± 0.16 | 0.02 ± 0.18 |
| 30 | 0.52 ± 0.18 | 0.05 ± 0.18 |
| 60 | 0.55 ± 0.16 | 0 ± 0.19 |
| 90 | 0.58 ± 0.19 | 0 ± 0.14 |
| 120 | 0.55 ± 0.18 | −0.03 ± 0.20 |

*ΔpH = pH value after teeth brushing − pH value before teeth brushing

As is well known, it is explained that dental caries take place because the organic acid (mainly, lactic acid) caused by decomposition and fermentation of carbohydrates dissolves the enamel material of teeth (decalcium), and it is reported that said decalcium takes place when the oral pH value is 5.4 or less. Therefore, dental caries may be prevented by maintaining the oral pH value at about 7 or more. In this connection, it is to be noted that according to another experiment carried out by the inventors of this application, the oral pH value may be lowered to 5.4 or less only by adding a trifling amount, i.e. 1 ml of lactic acid with a concentration of 0.2 ppm into the oral cavity. The chitin and the like used in the present invention, as is evident from Experimental Example 1, has a proper neutralizing ability against lactic acid, and further the dentifrice compound with chitin and the like, as is evident from Experimental Example, shows ability in the maintenance of the oral pH at a high value for a long time as compared with the control dentifrice free from said chitin and the like. It is safe to say that these experimental facts verify the effectiveness of chitin and the like for preventing the occurrence of dental caries.

Adding for cautions' sake, it is shown in Experimental Example 2 that the use of the dentifrice compounded with chitin and the like can maintain the oral cavity at a relatively high pH value for a long period of time. This is derived from the fact that the residence time of chitin and the like in the oral cavity is long. And, this fact is considered to be caused by the fact that chitin and the like, which are poly cations, are electrically bound at plural sites with the oral mucosa which exhibits an anionic property.

EXPERIMENTAL EXAMPLE 3

This example relates to the effects of chitosan and its malic acid salt for preventing the occurrence of periodontoclasia.

The back hair of a 6 weeks-old SIc-Wistar rat (male) was removed under nembutal anesthesia, sterilized by alcohol, and then inflicted thereon a 4 cm-long linear lacerated wound reaching to the hypodermal muscular membrane along the midline by means of a surgical knife. Then, the wounded portion was sewed together at intervals of 1 cm by means of a michel's clip, and said michel's clip was removed after lapse of 4 days. Medicines were applied on the whole wounded portion two times a day for 7 days continuously.

The rat was killed with chloroform on the 7th day after the formation of said wounded portion. The texture of said wounded portion was stripped off for sampling 3 skin pieces (width: 1 cm) intersecting the line of wound from each rat, and the tension required for separating the sewed up portion of the skin piece at the wounded portion was measured by means of the Instron tensile force measuring instrument. The average value was employed as a wound-healing indicator. The number of a group of rats was 6. As the control medicine there was employed a physiological saline.

The particulars of the medication used and the relation between the dosage and the groups of rats are shown in Table 3, and the relation between the groups of rats and the wound-healing effect (tensile strength) is shown in Table 4. In this connection, it is to be noted that the ratios shown in Table 4 were expressed as the relative values against the tensile strength of Group A evaluated as 100.

TABLE 3

| Group of rats | Medicine used | Dosage |
|---|---|---|
| A | 70% alcohol | 0.25 ml/time, injection |
| B | physiological salt-water (control) | " |
| C | aluminum dihydroxy allantoinate 1% ointment base *1 99% | 0.25 g/time, application |
| D | chitosan *2 1% ointment base *1 99% | " |
| E | aqueous chitosan salt solution *3 | " |

*1 "Dispensing guide line" edited by The Japan Pharmaceutical Association the revised third edition by Yakuginippo Ltd., Confer page 115
*2 REGITEX-NA-500.
*3 The aqueous solution obtained by dissolving 1 g of REGITEX-NA-500 in 100 ml of aqueous 1% malic acid solution.

TABLE 4

| Rat group | Initial weight (g) | Tensile strength (g/cm) | Ratio (%) |
|---|---|---|---|
| A | 137.0 ± 1.3 | 375.6 ± 28.5 | 100 |
| B | 133.3 ± 4.8 | 373.3 ± 21.8 | 99 |
| C | 133.8 ± 8.6 | 477 ± 50.1 | 127 |
| D | 132.5 ± 5.1 | 499 ± 30.5 | 133 |
| E | 132.6 ± 4.1 | 488.3 ± 25.1 | 130 |

It is said that the medicines having cell activating action (wound-healing effect) are effective for the purpose of medical therapy of periodontoclasia. Allantoin type medicines are well known as having cell activating action. Allantoin, aluminium chlorohydroxy allantoinate, aluminium dihydroxy allantoinate and the like have usually been used. The chitosan and chitosan salt used in the present invention, as is apparent from the results shown in Table 4, exhibit the medical effects which are superior to that of aluminium dihydroxy allantoinate in respect of the wound-healing effect. Accordingly, it can be understood that the chitosan and chitosan salt are effective for preventing periodontoclasia. It is further added that in the medicines of allantoin type, as their decomposition is accelerated at the alkali side, there is the problem that when said medicines are compounded for instance with a dentifrice, the range of forming agents and the like usuable therein is restricted. In the case of chitosan and chitosan salt, contrarily, there is no possibility of undergoing the above mentioned restriction because said chitosan and chitosan salt are chemically stable.

EXPERIMENTAL EXAMPLE 4

This is the experimental example concerning the effect of chitosan on the prevention of mouth odor.

Chitosan Lot No. 2200 (molecular weight: 88000, deacetylation degree: 77%) produced by Bioshell Inc. (635 Water Ave. E., Albany, Oreg. 97321) was pulverized, and sifted through a 200-mesh sieve. The chitosan particles that passed through said sieve were tested. 20 g of 1% chitosan suspension was accurately weighed in a 50-ml wide mouthed bottle, and a fixed amount of aqueous methyl mercaptan (1.5 ppm) solution was added thereto. Then, the bottle was corked tightly up and was left standing in a constant temperature bath at 37° C. for 5 minutes. Thereafter, the sample bottle was opened and the odor present in the head space of the bottle was subjected to sense evaluation for measuring the adsorption capacity of chitosan against methyl mercaptan. The examination values obtained by sense evaluation, as shown in Table 5, were expressed according to 5 rating method wherein the examination value 1 denotes the odor of 0.015 ppm of methyl mercaptan concentration, 3 denotes the odor of 0.045 ppm of methyl mercaptan concentration, 5 denotes the odor of 0.15 ppm of methyl mercaptan concentration and the intermediate odor therebetween was evaluated 2 and 4 respectively. Table 5 also shows the relation between each examination value and the mouth odor of said subject.

TABLE 5

| Examination value | Methyl mercaptan concentration | Correlation with the mouth odor of human |
|---|---|---|
| 1 | 0.015 ppm | slightly smelled |
| 3 | 0.045 ppm | smelled |
| 5 | 0.15 ppm | heavily smelled |

TABLE 6

| Amount of methyl mercaptan added (ppm) | 1.5 | 3.0 | 4.5 | 6.0 | 7.5 | 9.0 | 10.5 | 12.0 | 13.5 | 15.0 | 16.5 | 18.0 | 19.5 | 21.0 |
|---|---|---|---|---|---|---|---|---|---|---|---|---|---|---|
| Examination value | 0 | 0 | 0 | 0 | 1 | 1 | 2 | 3 | 3 | 3 | 3 | 4 | 4 | 5 |

90% or more of the substances causing the mouth odor are considered to be methyl mercaptan and hydrogen sulfide. As is evident from Table 6, however, the chitosan and the like used in the present invention completely adsorb the odor containing methyl mercaptan in the concentration up to 6 ppm. Taking into consideration the fact that the human odor threshold value to the odor of methyl mercaptan is 0.001 ppm or more, it can be clearly seen that chitosan and the like are extremely effective for prevention of the mouth odor.

Still further, the concrete oral compositions according to the present invention will be shown in examples. Every ingredient shown in examples is wt.%.

EXAMPLE 1

This example shows the formulation of tooth paste.

|  | A | B | C |
|---|---|---|---|
| calcium phosphate, dibasic | 50% | 20% | 45% |
| sorbitol | 20 | 20 | 20 |
| sodium lauryl sulfate | 1.5 | 2 | 1.5 |
| chitin | — | 40*2 | 3*2 |
| chitosan | 1*1 | — | 2*3 |
| carboxymethyl cellulose | 1 | 1.5 | 1 |
| saccharin | 0.1 | 0.1 | 0.1 |
| perfume | 1 | 1 | 1 |
| methyl para-hydroxybenzoate | — | 0.02 | 0.015 |
| water | balance | balance | balance |
| Total | 100 | 100 | 100 |

*1REGITEX-NA-50 (particles passed through a 200-mesh sieve)
*2REGITEX-FX (particles passed through a 200-mesh sieve)
*3REGITEX-NA-500 (particles passed through a 200-mesh sieve)

|  | D | E | F |
|---|---|---|---|
| calcium phosphate, dibasic | 50.0% | — | — |
| calcium pyrophosphate | — | 50.0% | — |
| amorphous silicic anhydride | — | — | 20.0% |
| sorbitol | 20.0 | — | 30.0 |
| glycerine | — | 20.0 | 25.0 |
| sodium lauroyl sarcosinate | 2.0 | 2.0 | 2.0 |
| chitosan salt | *4 4.0 | *5 2.0 | *6 6.0 |
| saccharin | 0.1 | 0.1 | 0.1 |
| perfume | 0.9 | 0.9 | 0.9 |
| water | balance | balance | balance |
| Total | 100 | 100 | 100 |

*4 denotes the amount of solids used from the solid content (10 g) of the solution obtained by dissolving 5 g of chitosan in 100 ml of aqueous 5% acetic acid solution.
*5 denotes the amount of solids used from the solid content (10 g) of the solution obtained by dissolving 5 g of chitosan in 100 ml of aqueous 5% lactic acid solution.
*6 denotes the amount of solids used from the solid content (10 g) of the solution obtained by dissolving 5 g of chitosan in 100 ml of aqueous 5% citric acid solution.

The tooth paste having Composition F was transparent, and when having made 10 panels compare the former (the tooth paste having the same composition as this tooth paste except that the chitosan salt was omitted) with the latter (the tooth paste having Composition C) every panel estimated that the latter did not taste rough as compared with the former. This fact implies that the addition of chitosan salt has suppressed the rough taste caused by amorphous silicic acid (silica).

EXAMPLE 2

This example shows the formulation of liquid dentifrice.

|  | A | B |
|---|---|---|
| glycerine | 35% | 35.0 |
| sodium polyacrylate | 5 | 5.0 |
| sodium monofluorophosphate | 0.76 | 0.76 |
| polyglycerine fatty acid ester | — | 1.5 |
| paraffin sulfonate | 1.5 | — |
| potassium phosphate, dibasic | 0.1 | 0.1 |

-continued

|  | A | B |
|---|---|---|
| potassium phosphate, monobasic | — | 0.2 |
| sodium phosphate, monobasic | 0.2 | — |
| chitin *7 | 0.5 | — |
| chitosan salt *8 | — | 6.0 |
| saccharin | 0.1 | 0.1 |
| perfume | 1 | 1.0 |
| water | balance | balance |
| Total | 100 | 100 |

*7 The watersoluble chitin (deacetylation degree: 48%) prepared based on the method of Sannan T and others [Confer Makromol. Chem., 176, 1191 (1975)].
*8 The amount of solids used from the solid content (10 g) of the solution obtained by dissolving 5 g of chitosan in 100 ml of aqueous 5% of malic acid solution.

EXAMPLE 3

This example shows the formulation of tooth powder.

|  | A | B |
|---|---|---|
| calcium carbonate, precipitated | — | 55% |
| aluminium hydroxide | — | 20 |
| chitin *2 | 90% | 15 |
| chitosan *1 | — | 5 |
| calcium phosphate, dibasic | 5 | — |
| perfume | 1 | 0.8 |
| saccharin | 0.2 | 0.2 |
| sodium lauryl sulfate | 1.5 | 1.5 |
| water | balance | balance |
| Total | 100 | 100 |

*1, *2 Confer Example 1

EXAMPLE 4

This example shows the formulation of mouth rinse.

|  | A | B | C | D |
|---|---|---|---|---|
| ethyl alcohol (90%) | 20% | 20% | 20% | 20% |
| sodium lauryl sulfate | 0.5 | — | 0.5 | — |
| sodium α-olefinsulfonate | — | 0.3 | — | — |
| sodium lauroyl sarcosinate | — | — | — | 0.5 |
| saccharin | 0.1 | 0.1 | 0.1 | 0.1 |
| perfume | 1 | 1 | 1 | 1 |
| chitin *7 | 0.5 | — | 0.5 | — |
| chitosan *8 | — | 1 | 10 | — |
| chitosan salt *6 | — | — | — | 2 |
| sodium monofluorophosphate | 0.15 | — | — | 0.15 |
| sodium phosphate, dibasic | 0.3 | 0.3 | — | 0.3 |
| sodium phosphate, monobasic | 0.7 | 0.7 | — | 0.7 |
| water | balance | balance | balance | balance |
| Total | 100 | 100 | 100 | 100 |

*6 Confer Example 1
*7 Confer Example 2
*8 watersoluble low-molecular chitosan (average polymerization degree: 7) prepared based on the method of Horowitz S. T. and others [Confer J. Am. Chem. Soc., 2218 (1958)]

EXAMPLE 5

This example shows the formulation of chewing gum.

|  | A | B | C |
|---|---|---|---|
| vinyl acetate type gum base | 25% | 30% | 25.0% |
| powdery sorbitol | 54.75 | — | 61.45 |
| 75% maltitol | 12 | 3 | 10.0 |
| calcium carbonate for food-additive | 2 | — | 2.0 |
| chitin *2 | 3 | 60 | — |
| chitosan *3 | 2 | — | — |
| chitosan salt *9 | — | — | 0.6 |
| talc | — | 5 | — |
| perfume | 1 | 1 | 1.0 |
| thau matin | 0.25 | 1 | 0.25 |
| food yellow No. 4 | very small amount | very small amount | very small amount |
| food red No. 3 | very small amount | very small amount | very small amount |
| Total | 100 | 100 | 100 |

*2, *3 Confer Example 1
*9 dried product of the solution obtained by dissolving 5 g of chitosan in 25 ml of aqueous 20% malic acid

EXAMPLE 6

This example shows the formulation of liquid oral freshener.

|  | A | B | C |
|---|---|---|---|
| ethyl alcohol (90%) | 30% | 30% | 30% |
| glycerine | 15 | 15 | 15 |
| perfume | 3 | 3 | 3 |
| chitosan *8 | 0.5 | 2 | — |
| chitin *7 | 0.5 | — | — |
| chitosan salt *10 | — | — | 1.6 |
| polyoxyethylene hydrogenated castor oil | 0.5 | 0.5 | 0.5 |
| saccharin | 0.2 | 0.2 | 0.2 |
| water | balance | balance | balance |
| Total | 100 | 100 | 100 |

*7, *8 Confer Example 4
*10 The amount of solids used from the solid content (10 g) of the solution obtained by dissolving 5 g of chitosan in 100 ml of aqueous 5% maleic acid

EXAMPLE 7

This example shows the formulation of solid oral freshener.

|  |  |
|---|---|
| peppermint oil | 1% |
| lemon oil | 0.2% |
| eugenol | 0.1 |
| anethole | 0.2 |
| carvone | 0.3 |
| chitin *2 | 20 |
| chitosan *1 | 25 |
| licorice powder | 30 |
| xylitol | 7 |
| orris powder | 4 |
| cinnamon powder | 3 |
| ginger powder | 2 |
| clove powder | 1 |
| gum arabic liquid | balance |
| Total | 100 |

The solid oral freshener shown in thus example was prepared by well pulverizing the solid raw material into powder and mingling, adding the liquid material thereto and kneading together, and making the same into particles.

We claim:
1. A composition for reducing dental caries, periodontoclasia and mouth odor, comprising an amount of at least 0.01 wt.% of a material selected from the group consisting of chitin, chitosan, pharmaceutically acceptable acid salts of chitosan and mixtures thereof, effective to reduce the incidence or severity of dental caries, periodontoclasia and mouth odor, said material being compounded in a dentifrice, toothpaste, tooth powder, liquid dentifrice, mouth rinse, oral freshener or chewing gum composition.

2. A composition for reducing dental caries, periodontoclasia and mouth odor, comprising a material selected from the group consisting of chitin, chitosan, pharmaceutically acceptable acid salts of chitosan and mixtures thereof, in an amount of at least 0.01 wt.%, effective to reduce the incidence or severity of dental caries, periodontoclasia and mouth odor, in association with a pharmaceutically acceptable dentifrice composition.

3. A composition as claimed in claim 1 in which said composition is a toothpaste containing from 0.01 to 70 wt.% of chitin, chitosan or mixture thereof.

4. A composition as claimed in claim 1 in which said composition is a tooth powder containing from 0.01 to 97 wt.% of chitin, chitosan or mixture thereof.

5. A composition as claimed in claim 1 in which said composition is a solid oral freshener containing from 0.01 to 70 wt.% of chitin, chitosan or mixture thereof.

6. A composition as claimed in claim 1 in which said composition is a liquid composition containing from 0.01 to 20 wt.% of chitin, chitosan or mixture thereof.

7. A composition as claimed in claim 1 in which said composition is a chewing gum containing from 0.01 to 60 wt.% of chitin, chitosan or mixture thereof.

8. A composition as claimed in claim 1 effective for treating periodontoclasia containing at least about 0.01 wt.% of a pharmaceutically acceptable acid salt of chitosan.

9. A composition as claimed in claim 8 in which said acid salt is the hydrochloric acid salt of chitosan.

10. A composition as claimed in claim 8 in which said acid salt is selected from the group consisting of the acetic acid, lactic acid, citric acid, malic acid and maleic acid salts of chitosan.

* * * * *